(12) United States Patent
Kuster

(10) Patent No.: US 10,517,837 B2
(45) Date of Patent: Dec. 31, 2019

(54) PROCESS FOR OBTAINING A SYSTEM FOR THE CONTROLLED DELIVERY OF A BIOLOGICALLY ACTIVE SUBSTANCE AND CONTROLLED DELIVERY SYSTEM OBTAINED THEREBY

(71) Applicant: SUNtekna sagl, Ghirone-Blenio (CH)

(72) Inventor: John Kuster, Klagenfurt am Worhersee (AT)

(73) Assignee: SUNTEKNA SAGL, Ghirone-Blenio (CH)

( * ) Notice: Subject to any disclaimer, the term of this patent is extended or adjusted under 35 U.S.C. 154(b) by 0 days.

(21) Appl. No.: 15/548,963

(22) PCT Filed: Feb. 2, 2016

(86) PCT No.: PCT/IB2016/050518
§ 371 (c)(1),
(2) Date: Aug. 4, 2017

(87) PCT Pub. No.: WO2016/125077
PCT Pub. Date: Aug. 11, 2016

(65) Prior Publication Data
US 2018/0028460 A1 Feb. 1, 2018

(30) Foreign Application Priority Data

Feb. 6, 2015 (IT) ............................. TO2015A0083

(51) Int. Cl.
*A61K 9/70* (2006.01)
*A61K 47/36* (2006.01)

(52) U.S. Cl.
CPC ............ *A61K 9/7007* (2013.01); *A61K 47/36* (2013.01)

(58) Field of Classification Search
CPC ............................. A61K 47/36; A61K 9/7007
See application file for complete search history.

(56) References Cited

U.S. PATENT DOCUMENTS 7,357,955 B2 * 4/2008 Shen .......................... A23J 3/16
426/590

FOREIGN PATENT DOCUMENTS

EP 0867470 * 9/1995 ................ C08L 5/00

OTHER PUBLICATIONS

Of Choonara et al. (Journal of pharmaceutical sciences, vol. 98, No. Jun. 2009 pp. 2059-2072).*
Lee et al. (Macromolecules 2000, 33, 97-101).*
Miyata et al. (Macromol. Chem. Phys. 197, 1135-1146, 1996.*
(Analysis of Hydrolysis Yields by Using Different Acids for Bioethanol Production for Brazilian Woods, XVII International Conference of Industrial Engineering and Operations Management, Oct. 2011). (Year: 2011).*
Sletmoen et al. (Macromol. Symp 2010, 291-292,345-353). (Year: 2010).*
Choonara Yahya et al., "Mechanistic Evaluation of Alginate-HEC Gelisphere Compacts for Controlled Intrastriatal Nicotine Release in Parkinson's Disease", Journal of Pharmaceutical Sciences, vol. 98, Issue No. 6, pp. 2059-2072, Jun. 2009 (Abstract only).
Dilipkumar Pal et al., "Development, Optimization, and Antidiabetic Activity of Gliclazide-Loaded Alginate-Methyl Cellulose Mucoadhesive Microcapsules", AAPS PharmSciTech, vol. 12, Issue No. 4, pp. 1431-1441, Oct. 2011 (Abstract only).
Banerjee Subham et al., "Trivalent Ion Cross-linked pH Sensitive Alginate-methyl Cellulose Blend Hydrogel Beads from Aqueous Template", International Journal of Biological Macromolecules, vol. 57, pp. 297-307, Jun. 2013 (Abstract only).
Kuen Yong Lee et al., "Degradation Behavior of Covalently Cross-Linked Poly(aldehydeguluronate) Hydrogels", Macromolecules, vol. 33, No. 1, pp. 97-101, Jan. 2000 (Abstract only).

* cited by examiner

*Primary Examiner* — Anna R Falkowitz
(74) *Attorney, Agent, or Firm* — Howson & Howson LLP

(57) ABSTRACT

The present invention relates to a process for obtaining a system for the controlled delivery of a biologically active substance allowing to obtain an effective delivery in terms of percentage of said biologically active substance that is absorbed by the organism. More particularly, the present invention relates to a process consisting in obtaining a controlled delivery system in which the biologically active substance is enclosed in a structure having a substantially parallelepiped shape with the desired shape and size, which can internally adapt to the biologically active substance to be carried and externally to the interaction with target cells (for example, enterocytes), thus optimizing the delivery modes of said biologically active substance. Advantageously, the process according to the invention allows to create parallelepiped structures with nanometric, micrometric or larger sizes, thereby making the controlled delivery system thus obtained suitable for a large variety of biologically active substances, including ions, molecules and macromolecules.

12 Claims, 7 Drawing Sheets

PROCESS FOR OBTAINING A SYSTEM FOR THE CONTROLLED DELIVERY OF A BIOLOGICALLY ACTIVE SUBSTANCE AND CONTROLLED DELIVERY SYSTEM OBTAINED THEREBY

TECHNICAL FIELD

The present invention relates to a process for obtaining a system for the controlled delivery of a biologically active substance. More particularly, the present invention relates to a process for obtaining a system that allows to obtain an effective delivery with respect to the percentage of biologically active substance that is absorbed by the organism.

The present invention further relates to a system for the controlled delivery of a biologically active substance made according to said process.

PRIOR ART

Biologically active substances, such as drugs, food supplements and the like, which are taken through the oral route, are known and very widespread.

In order for such biologically active substances to properly exert their effect, they must reach the desired part of the digestive tract or of the target organ in the desired amount. The amount of biologically active substance released to the desired site for its action depends on the dosage, on the absorption rate and on the distribution of such absorption in the body; the effect will cease when the concentration of biologically active substance drops below a minimum threshold because of excretion and metabolism.

In particular, it is desirable that some biologically active substances remain intact while passing through the first part of the digestive tract (oral cavity, esophagus, stomach), so that they can be delivered to the organism only in the intestinal tract.

Biologically active substances are seldom administered alone. On the contrary, they are usually administer in the form of formulations that, besides the biologically active substance (or possibly a combination of biologically active substances), comprises one or more excipients which can have different function, including those of facilitating preparation and administration of the biologically active substance, promoting its bioavailability, protect it against deterioration and so on.

In particular, excipients may potentially influence the rate and amount of absorption of the biologically active substance. For example, non-toxic, biocompatible polymers can be used as excipients for influencing delivery of biologically active substances.

Use of alginates for this purpose is widespread in prior art. Alginates are salts of the alginic acid, which is a natural polysaccharide and a linear polymer consisting of G groups (guluronic acid) and M groups (mannuronic acid) arranged in blocks in the polymer chain.

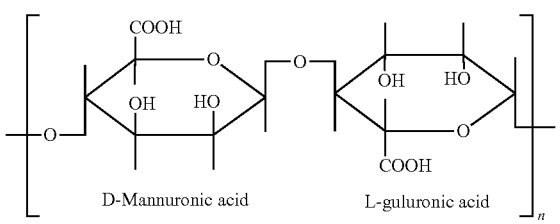

The proportion between G blocks and M blocks may vary depending on the source from which the alginates derive.

Hydration of alginic acid and alginate causes swelling thereof and formation of a high-viscosity gel, which enables them to play a significant role in systems for the controlled delivery of biologically active substances.

Indeed, if the formulation comprises a core containing the biologically active substance and an outer coating containing alginates, once the alginates are hydrated, they will form a barrier between the biologically active substance and the organism, thus allowing to control delivery of said biologically active substance.

The delivery of the biologically active substance is indeed modulated by the diffusion of said substance through swelling of the polymer matrix and by the process of dissolution/erosion at the periphery of the matrix.

In particular, polymer matrices containing alginates have proved useful as excipients for biologically active substances that have to remain intact while passing through the stomach and be delivered to the intestinal tract.

However, the process of swelling and dissolution/erosion is very complex, which makes it extremely difficult to obtained a delivery of the biologically active substance that is reproducible and has a predictable kinetics.

This problem is worsened by the fact that, according to prior art, formulations containing the biologically active substance are provided in the form of spheres or "beads", whereby the core of the biologically active substance is enclosed within a barrier having a uniform thickness.

The presence of a barrier with a uniform thickness through which the biologically active substance must diffuse further increases the difficulty in obtaining a delivery system having a reproducible and predictable kinetics.

This turns out, moreover, in the risk of a poor absorption efficiency of the biologically active substance in terms of percentage of substance actually absorbed by the organism.

In order to overcome these drawbacks, it is usual to increase dosage of the biologically active substance with respect to the dosage that would be theoretically necessary.

This solution, however, is not free of contraindications, with particular reference to the occurrence of undesirable side effects and/or to the onset of intolerance to the biologically active substance in question.

The main object of the present invention is therefore to provide a system for the controlled delivery of a biologically active substance which allows to overcome the drawbacks mentioned above and to obtain a predictable and reproducible kinetics of delivery and, in the end, to improve the efficiency of absorption of said biologically active substance in terms of percentage of absorbed substance.

These and other objects are achieved with the process for obtaining a system for the controlled delivery of a biologically active substance and with the controlled delivery system obtained thereby as claimed in the appended claims.

DISCLOSURE OF THE INVENTION

The basic concept of the present invention is to obtain a controlled delivery system in which the biologically active substance, instead of being enclosed in a polymer matrix having a substantially spherical shape, is enclosed in a structure having a substantially parallepiped shape.

In other words, suitable polymers are used not for forming a substantially spherical matrix around the core containing the biologically active substance, but for forming the walls of a substantially parallelepiped (or cubical) structure or "box" in which the biologically active substance is introduced, the size of said structure or "box" being adjustable according to the substance to be included therein.

According to the invention, this structure or "box" is devised so that one or more wall(s) open(s) so as to make the biologically active substance immediately available when the formulation reaches the desired delivery site, thus improving the efficiency of absorption of said biologically active substance in terms of percentage of absorbed substance.

In particular, said structure or "box" can be devised for opening when a preset parameter—such as the pH—reaches a predetermined value; alternatively, it can be devised so as to be phagocytized and open in the cell cytoplasm.

By way of example, it is possible to provide that the structure or "box" remain closed under acid pH conditions, so as to protect the biologically active substance during passage through the stomach, and open and make the substance available to the organism as soon as it reaches the intestine, under neutral pH conditions.

The inventive principle of the present invention can be worked by implementing the process for obtaining a controlled delivery system as claimed, which process essentially provides for forming a plurality of mutually parallel, flat polymer structures that are connected to one another by bridges that are also made with polymers and allow to obtain the three-dimensional structure with a parallelepiped shape.

This tridimensional structure with parallelepiped shape can form by itself the system for the controlled delivery of the biologically active substance or it can be used for forming one or more—preferably all—the walls of a "box", this too with a substantially parallelepiped shape, which receives the biologically active substance.

Said flat, parallel polymer structures can be obtained by acid hydrolysis of alginates or similar polysaccharides with appropriate polyprotic acids, either inorganic or organic, whereas the bridges can be obtained by means of monomers or polymers of cellulose substituted with one or more functional groups or of analogous polysaccharides.

The process according to the invention allows to make structures or "boxes" having the desired shape and size, which can adapt internally to the biologically active substance to be carried and externally to the interaction with the target cells (for example, enterocytes), thus making the carried substance bioavailable with greater possibility of absorption or passage through the paracellular pathway or of immediate use upon absorption.

This makes it possible to avoid an increase in the dosage of the biologically active substance, to better modulate the absorption, to improve the pharmacokinetics and the pharmacodynamics and, thus, to improve the efficiency of action of the biologically active substance while at the same time reducing the risk of side-effects.

Advantageously, the process according to the invention allows to make structure or "boxes" of any size, and particularly of nanometric, micrometric or larger sizes. Advantageously, this allows to use the process of the invention for obtaining systems for the controlled delivery of biologically active ions, molecules or macromolecules.

BRIEF DESCRIPTION OF THE DRAWINGS

Characteristics and advantages of the invention will become more apparent from the following detailed description of a preferred embodiment of the invention, given by way of non-limiting example with reference to the annexed drawings, in which.

DESCRIPTION OF A PREFERRED
EMBODIMENT OF THE INVENTION

Figure 1:
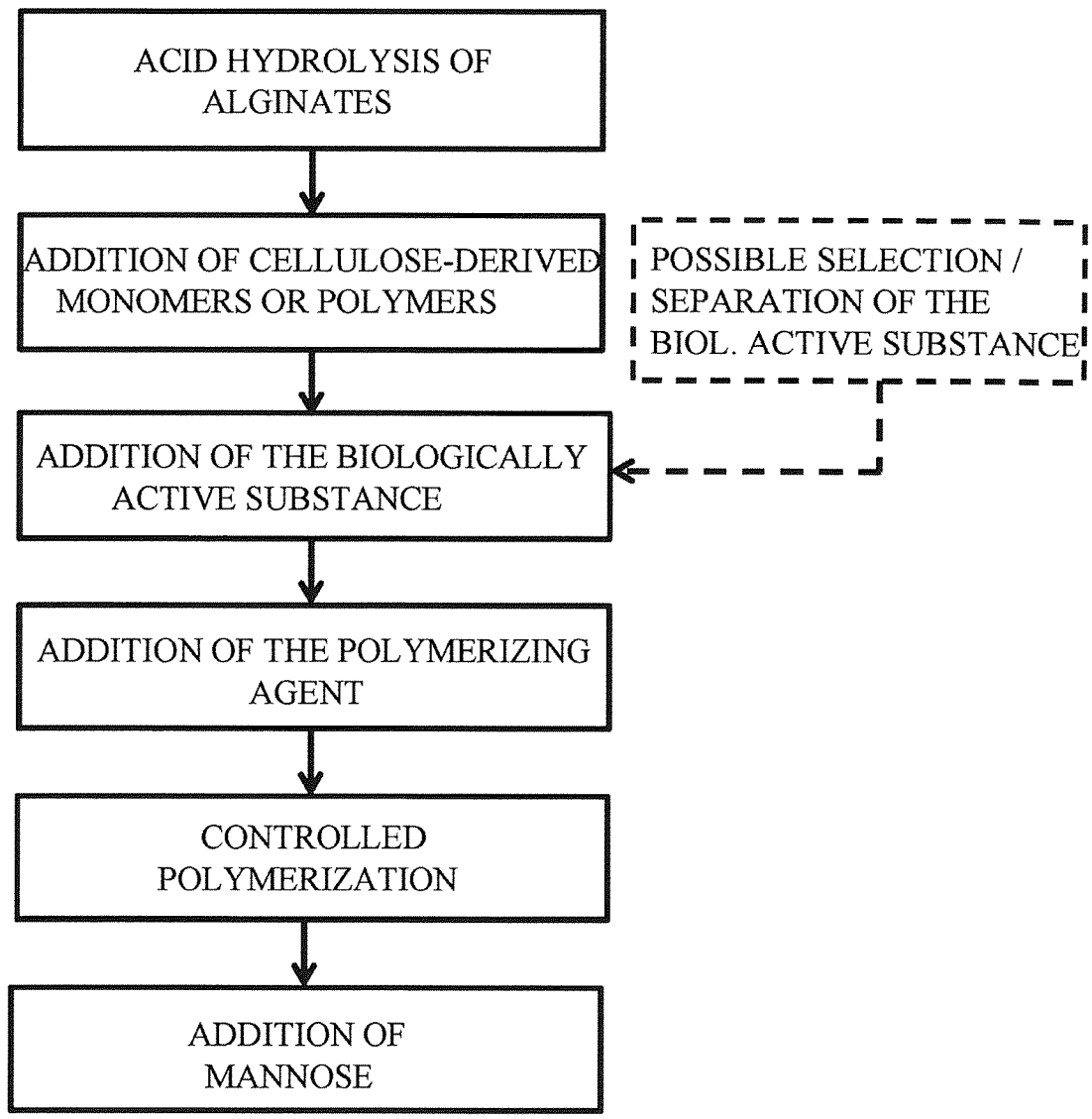
FIG. 1 is a block diagram showing the main steps of the process for obtaining a system for the controlled delivery of a biologically active substance according to the invention.

Referring at first to FIG. 1, the main steps of the process according to the invention for obtaining a system for the controlled delivery of a biologically active substance are illustrated in the form of block diagrams.

In a first step of said process, alginates or analogous polysaccharides are subjected to a hydrolysis process in an acid environment.

The Applicant has surprisingly found that by using a polyprotic acid, more particularly phosphoric acid, it is possible to obtain, at the end of the step of hydrolysis of the alginates, polymer chains which may form flat structures substantially in the form of sheets.

Instead of phosphoric acid it is possible to use other polyprotic acids, either inorganic or organic, for example lactic acid.

The results of this first step of the process are strongly dependent not only on the starting alginate, but also on the conditions under which the hydrolysis process is carried out—in particular in terms of temperature—as well as on the timing of the process itself.

In a preferred embodiment of the invention, the hydrolysis process is carried out at a temperature ranging between 12 and 70° C., and preferably between 37 and 65° C., for a time ranging between 1 h and 78 h, and more preferably between 10 h and 26 h.

Figure 2A:
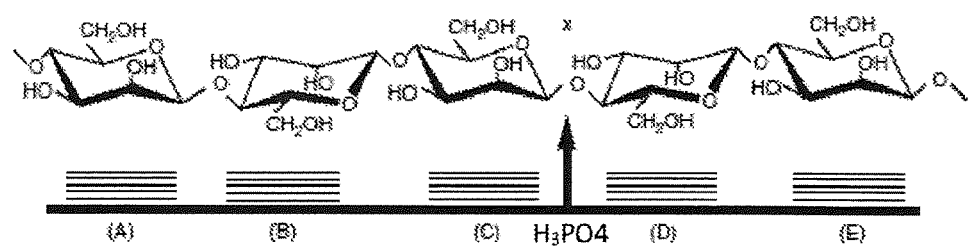
FIGS. 2a-2b show the action of polyprotic acid during the hydrolysis step and the resulting structure.

FIG. 2a schematically shows the reaction of depolymerization of an alginate by means of phosphoric acid at 50° C. for 24 hours, with consequent separation of G groups and M groups.

Figure 2B:
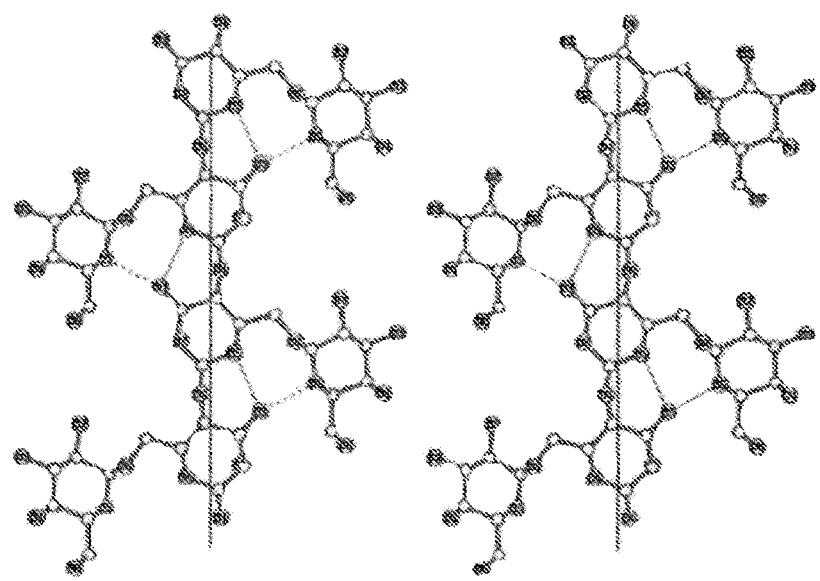

FIG. 2b schematically shows flat structures or "sheets" of G groups and M groups resulting from hydrolysis of the alginate by means of phosphoric acid. Advantageously, by using phosphoric acid (or another polyprotic acid) it is possible to obtain flat specular structures forming parallel walls of the parallelepiped structure or "box" in which the active substance will be introduced. In a second step of the process according to the invention, monomers or polymers of cellulose substituted with functional groups or analogous polysaccharides are added; this addition has the purpose of ensuring that the subsequent construction is oriented in space during the formation of bonds between the G blocks and M blocks of alginate which have been formed as a consequence of hydrolysis. In particular, in a preferred embodiment of the invention, in this step the cellulose substituted with functional groups is cleaved into monomers or polymers, particularly dimers: said cellulose monomers or dimers form bridges for linking the chains of G blocks and M blocks of the alginate which form said sheet-like structures.

Among the monomers and polymers of cellulose substituted with functional groups that can be used in the process according to the invention, monomers and polymers of hydroxyethyl cellulose, methyl ethyl cellulose, methyl cellulose and propyl cellulose can be mentioned by way of non-limiting examples.

FIGS. 3a-3d are electron microscope images referring to a working example of the invention in which hydroxyethyl cellulose has been added to the starting alginate.

Figure 3A:
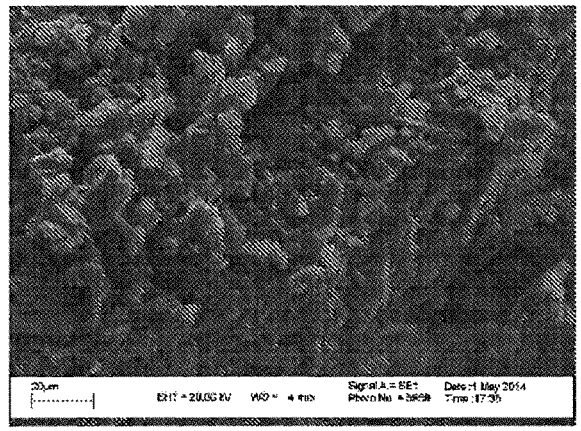
FIGS. 3a-3d are electron microscope images showing structures or "boxes" of different sizes obtainable by the process according to the invention.
Figure 3B:
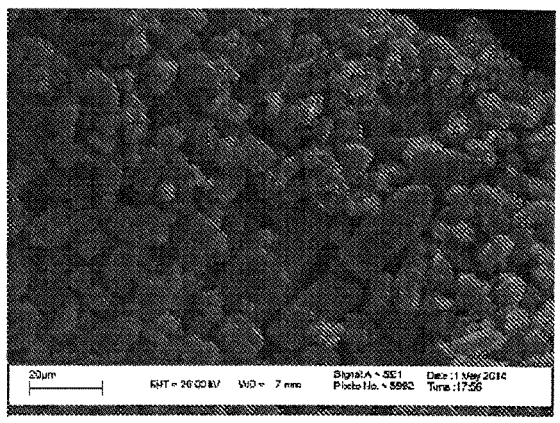
Figure 3C:
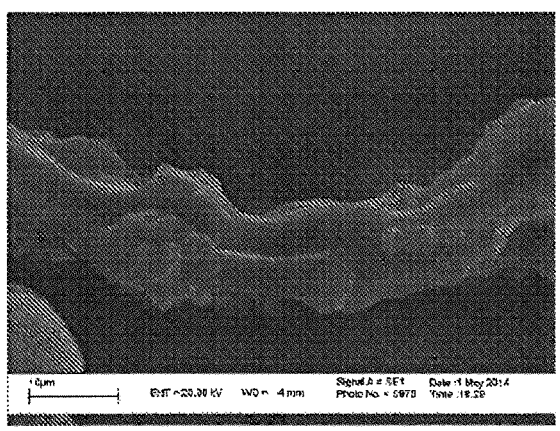
Figure 3D:
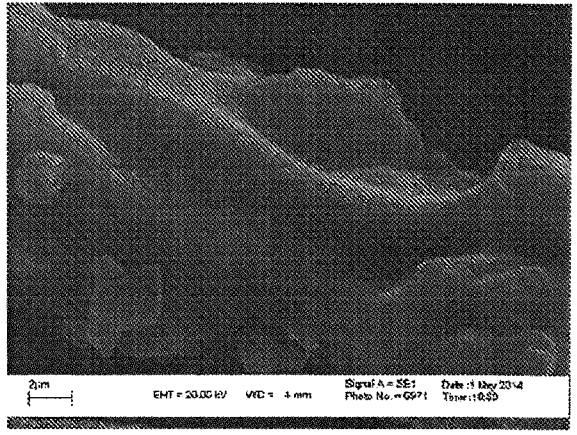

From a comparison, especially between FIGS. 3a-3b, it can be seen how structures or "boxes" of different sizes can be obtained by varying the starting alginate, the ratio between alginate and hydroxyethyl cellulose, and the reaction temperature.

In a third step of the process according to the invention, the biologically active substance—for example the drug—to be carried by the controlled delivery system is introduced.

The biologically active substance is assembled to the previously provided structure of G groups and M groups and cellulose bridges due to the surface charges.

For this purpose it is important that the surface charges of the biologically active substance are delocalized.

As anticipated above, said biologically active substance can be in the form of ions, molecules or macromolecules, because—as is also well visible in FIGS. 3a-3d—the process according to the invention allows to form structures or "boxes" of very different sizes, particularly of nanometric, micrometric or larger sizes.

If necessary—for example in the case where the biologically active substance is an ion—the step of introducing said biologically active substance can be preceded by a step of separation and selection of said substance.

For instance, if the biologically active substance is a calcium ion provided as a calcium salt, a preliminary step of separating and selecting the ion from the rest of the molecule, so that only the ion—i.e. the biologically active principle—is incorporated into the parallelepiped structure.

In a fourth step of the process according to the invention, polymerization of the products obtained from the previous hydrolysis step is effected by adding an appropriate polymerizing agent.

In a preferred embodiment of the invention, divalent ions, particularly calcium ions ($Ca^{2+}$) are used as polymerizing agent.

Use of calcium ions for the polymerization of alginates is known.

According to prior art, however, the polymerization of alginates by means of calcium ions always generates spherical structures.

In the process according to the invention, instead, thanks to the previous step of acid hydrolysis and to the subsequent addition of cellulosic forms acting as a "mold", the polymerization step generates flat structures, substantially in the form of sheets, consisting of chains of G blocks and M blocks of the alginate and cellulosic bridges interposed therebetween.

Accordingly, in the process according to the invention, the addition of calcium ions or similar divalent ions has the function of blocking the digestion reaction and at the same time modifying the size of the walls of the structure or "box", in particular their thickness. In a fifth step of the process according to the invention, mannose of the formula is introduced.

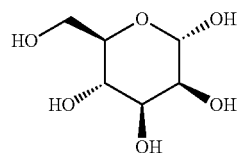 [SMILES: OC[C@H]1O[C@H](O)[C@@H](O)[C@@H](O)[C@@H]1O]

Mannose completes the three-dimensional structure of the structure or of the "box" enclosing the biologically active substance.

Owing to the fact that mannose is capable of shifting from a closed form to an open form depending on the conditions of the outer environment, it is possible to exploit this capability for protecting the biologically active substance from the outer environment or, on the contrary, for making it available to the organism in a more effective way than with a controlled delivery structure having a spherical configuration according to prior art.

It is apparent that mannose might be replaced with an analogous substance, provided that this, too, is capable of shifting from a closed form to an open form.

It is further apparent that this property of mannose can be exploited due to the fact that the controlled delivery system of the present invention is provided as a parallelepiped structure or "box": in this way, by shifting from the closed form to the open form, mannose (acting as a "hinge") allows opening of a wall of the structure or "box" and delivery of the biologically active substance. This result could not be achieved by merely adding mannose to a traditional delivery system.

In this manner, the process according to the invention allows to obtain a controlled delivery system which, depending on the conditions—for example, the pH value—of the surrounding environment, can open and deliver mannose and the biologically active substance carried by the system.

In particular, in a preferred embodiment of the process according to the invention, mannose retains the closed form in the presence of an acid pH and shifts to the open form in the presence of a neutral pH.

Figure 4:
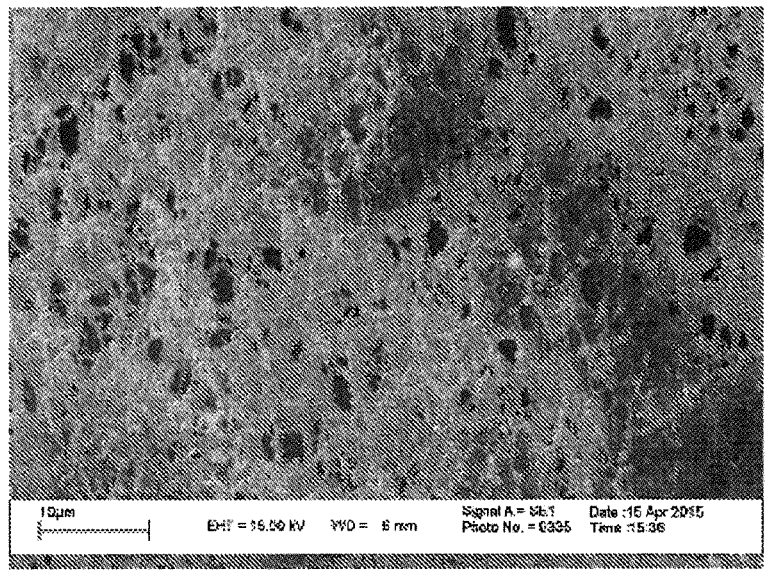
FIG. 4 shows the residual cellulose structure after opening of the structures or "boxes" of FIGS. 3a-3d and delivery of the biologically active substance.

In this manner, advantageously, the biologically active substance can pass intact (protected by the closed "box") through the gastric tract and be delivered to the intestine, as soon as the raise in the pH makes mannose shift from the closed form to the open form. FIG. 4 is an electron microscope image showing the degradation of the structures or "boxes" of the invention in the presence of a neutral pH, leaving only a cellulose skeleton. As mentioned above, the process according to the invention allows to create different structures, capable of adapting to a great variety of very different biologically active substances.

In particular, it is possible to create structures of nanometric, micrometric or larger sizes. In the case of biologically active substances with nanometric sizes, a structure formed by a pair of flat structures consisting of chains of G blocks and M blocks of the alginate and cellulosic bridges interposed therebetween constitutes per se the controlled delivery system in which the biologically active substance is contained.

Instead, in the case of biologically active substances with micrometric or larger sizes, the structure formed by the pair of flat structures consisting of chains of G blocks and M blocks of the alginate and cellulosic bridges interposed therebetween is used for providing one or more walls, and preferably all the walls, of a "box" which in turn has a substantially parallelepiped shape and the biologically active substance is introduced into said "box" defined by said walls.

With the process describe above, it is possible to create structures or "boxes" of nanometric, micrometric or larger sizes by modifying the process conditions.

For example:

in order to create structures with nanometric sizes it is possible to modify the time and temperature of the hydrolysis step while maintaining the acid concentration constant and by adding a very small amount of cellulose so that molecules become assembled so as to form small parallelepipeds of 1-100 nm containing solvates with electrostatic interactions with monovalent, divalent and trivalent metal ions or small molecules having a weakly positive or globally positive surface charge;

in order to create structures of micrometric sizes it is possibly to modify the time and temperature of the hydrolysis step while maintaining the acid concentration constant and by adding different amounts of cellulose either as hydroxyethyl cellulose (HEC) or as methyl ethyl cellulose (MEC) and by varying its configuration suitable for acting as a skeleton or frame for supporting the polymer sheets up to a size of 2-4 μm, with the possibility of containing organic macromolecules, also oxygen-reactive ones, by protecting their oxidation sites;

in order to create structures with macro sizes, supramolecular construction of the cellulose-alginate complex is used as a basis for defining cellulose direction by orienting polymerization so as to form tube-shaped hollow structures the wall of which is made of cellulose-alginate copolymers; use is made of the interaction of Mg ions with Ca ions in a well-defined proportion in order to proceed to assembling; the amounts of MEC and HEC added in this case require addition of gluconolactone and more complex sugars such as methylglucose distearate, which in trace amounts allows to keep macromolecular pieces separated, thus preventing them from self-assembling prior to introduction of the substance to be carried.

The process according to the invention may possibly comprise an optional stabilization step involving addition of a gelling agent such as, for instance, a polysaccharide such as inulin or cellulose or its derivatives.

Such stabilization step is particularly advantageous in the case of systems for the delivery of biologically active substances having micrometric or larger sizes.

In addition, said process may possibly comprise an optional further step in which the created structure or "box" is provided with a protective layer. Said protective layer can be obtained, for instance, by adding fructose or the like.

Finally, as indicated above, in the case of large-sized "boxes", the process according to the invention possibly comprises a step in which additives are added in order to keep macromolecular pieces separated, thus preventing them from self-assembling prior to introduction of the substance to be carried, said additives comprising gluconolactone and methylglucose distearate.

In addition or as an alternative to gluconolactone and methylglucose distearate, it would be possible to use a compound selected from galactose, gluconic acid, gluconic acid salts, gluconic acid esters or combinations thereof.

Figure 5:
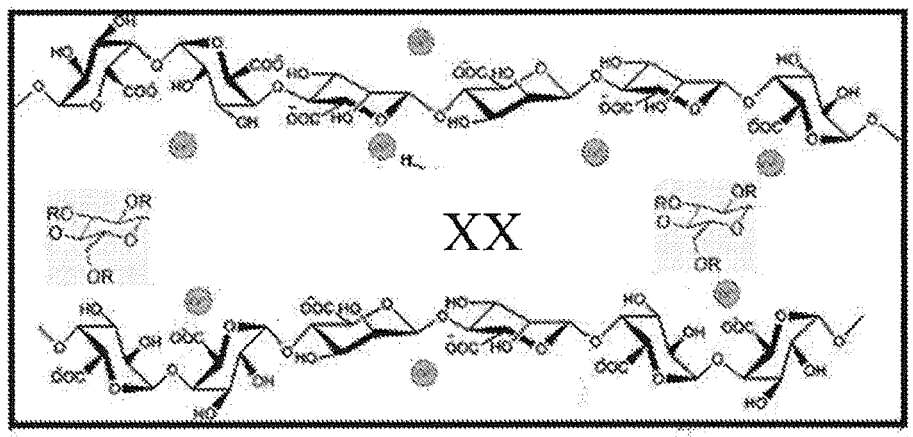
FIG. 5 schematically shows a structure of a controlled delivery system obtainable by the process of FIG. 1 and suitable for biologically active substances with nanometric size.

FIG. 5 shows very schematically an example of a structure of a controlled delivery system obtainable with the process described above and especially suitable for a biologically active substance with nanometric size.

In this case, the controlled delivery system consists of the structure comprising a pair of sheets of polymer chains of G blocks and M blocks and cellulosic bridges interposed therebetween.

As is visible in FIG. 5, the polymer chains of G blocks and M blocks arrange themselves in flat, parallel structures (arranged on the plane x-z in FIG. 5) and form bridging bonds due to the presence of calcium ions $Ca^{2+}$.

Among the structures of G blocks and M blocks there are provided bridges of cellulose monomers or polymers arranged along an axis perpendicular to the plane of the aforesaid polymer chains (axis y in FIG. 5); in particular, in FIG. 5 there are provided bridges of monomers of hydroxyethyl cellulose of the formula

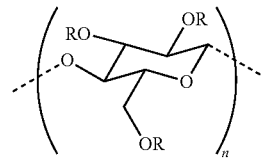

where R=H or R=$CH_2CH_2OH$.

Mannose (not shown in FIG. 5) inserts itself tridimensionally (on the axis z in FIG. 5). The biologically active substance XX is therefore enclosed within a tridimensional "box-like" structure. Electrostatic interactions become established among the G blocks and the M blocks and said biologically active substance, as well as among the G blocks and the M blocks and the monomers of hydroxyethyl cellulose, said interactions being kept balanced by mannose, which shifts from the open form to the closed form.

By shifting then from the closed form to the open form in the predetermined conditions, mannose causes opening of the sheets consisting of the polymer chains of G blocks and M block and allows effective delivery of the drug.

Figure 6:
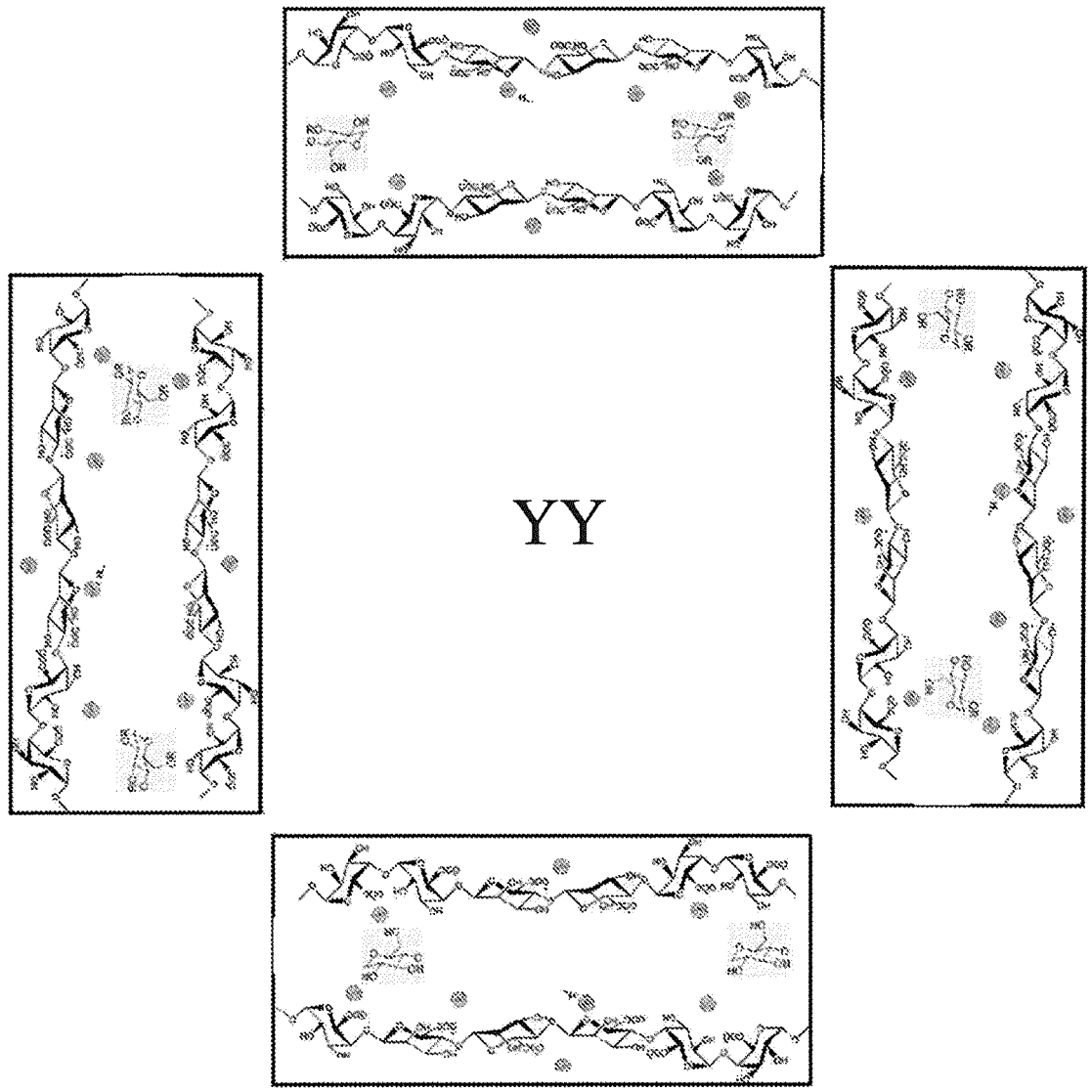
FIG. 6 schematically shows a structure of a controlled delivery system obtainable by the process of FIG. 1 and suitable for biologically active substances with micrometric or larger size.

FIG. 6, instead, shows very schematically an example of a controlled delivery system obtainable with the process described above and especially suitable for a biologically active substance with micrometric or larger size.

In this case, the structure comprising a pair of sheets of polymer chains of G blocks and M blocks and cellulosic bridges interposed therebetween constitutes each of the walls of which the "box" forming the controlled delivery system is made.

As is visible in FIG. 6, the biologically active substance YY is therefore enclosed within said tridimensional "box" in which each wall has the structure shown in FIG. 5.

Mannose inserts itself along the edges between the different walls and electrostatic interactions become established among the G blocks and M blocks and said biologically active substance, as well as among the G blocks and M blocks and the monomers of hydroxyethyl cellulose, said interactions being kept balanced by mannose, which shifts from the open form to the closed form.

By shifting then from the closed form to the open form in the predetermined conditions, mannose causes opening of the sheets consisting of the polymer chains of G blocks and M blocks and allows effective delivery of the drug.

Besides improving efficiency in delivering the biologically active substance, the invention allows to obtain bioavailable substances with very low manufacturing costs with respect to the processes of prior art.

Furthermore, use of alginates associated to mannose allows to produce a high-quality end product with a well-known additional final effect thanks to the well-known antibacterial/bacteriostatic properties of mannose.

APPLICATION EXAMPLES

Some examples of application of the process according to the invention are given below.

Example 1—Preparation of a Controlled Delivery System with Nanometric Size (55-100 nm)

1-90 gr of alginate are added to one liter of osmotized water brought to 5-70° C. Complete dissolution is reached in 1-10 h.

Then the hydrolysis step starts. 5-50 g phosphoric acid are added and stirring is carried out for 1-26 hours. 1.50-1500 gr HEC and/or MEC are added and stirring is carried out slowly, but also vigorously for further 1-60 h. Cooling to 4-27° C. is effected and the pH is controlled by adjusting it from 2 to 12 by means of NaOH.

The assembling step is then carried out. 0.01-100 gr aldose epimers on chiral and non-chiral C2 C3 C4, but also ketose with the same characteristics are added. Temperature is adjusted to 1-60° C. and mixing is effected under very vigorous stirring for 12 h. Temperature is brought back to 2-29° C. The desired amount of biologically active substance is added and mixing is carried out at 1-72° C. for a time comprised between 1 min and 24 h.

0.00001-100 gr Ca ions with anions of the halogen series are added; 0.00001-100 gr Mg ions with anions of the halogen series are added; 0.00001-100 gr Sr ions with anions of the halogen series are added.

Example 2—Preparation of a Controlled Delivery System with Micrometric Size

Hydrolysis step: 0.0011-50 gr phosphoric acid are added to different forms of sodium and potassium alginates and vigorous stirring is effected for 1-5 h; 1.50-1500 gr HEC and/or MEC are added and stirring is effected slowly, but also vigorously for further 1-60 h; cooling to 4-27° C. is effected and the pH is controlled by adjusting it from 2 to 12 by means of NaOH.

Assembling step: 0.01-100 gr aldose epimers on chiral and non-chiral C2 C3 C4 but also ketose with the same characteristics are added; temperature is adjusted to 1-60° C. and mixing is carried out under very slowly, but also very vigorous stirring for 12 h; temperature is brought back to 2-29° C.; the desired amount of biologically active substance is added and mixing is carried out at 1-72° C. for a time comprised between 1 min and 12 h; 0.00001-100 gr Ca ions with anions of the halogen series are added; 0.00001-100 gr Mg ions with anions of the halogen series are added; 0.00001-100 gr of Sr ions with anions of the halogen series are added.

Example 3—Preparation of a Controlled Delivery System with Macro Size 5-50 gr polyprotic acid are added to 0.5-100 gr alginate and stirring is carried out slowly, but also vigorously for 1-5 h; 1.50-1500 gr HEC and/or MEC are added and stirring is carried out slowly, but also vigorously for further 1-60 h; 0.0001-90 gr gluconolactone and 0.0001-100 gr inulin are added; cooling to 4-27° C. is effected and the pH is controlled by adjusting it from 2 to 12 by means of NaOH; a dimer, but also a tetramer of an aldose or chetose, but also an ester of the monomer or dimer in an amount variable from 0.00001 to 70 g.

0.01-100 gr aldose epimers on chiral and non-chiral C2 C3 C4 but also ketose with the same with the same characteristics are added; temperature is adjusted to 1-60° C. and mixing is effected under very vigorous stirring for 12 h; temperature is brought back to 2-29° C.; the desired amount of biologically active substance is added and mixing is carried out at 1-72° C. for a time comprise between 1 min and 2 h; 0.00001-100 gr Ca ions with anions of the halogen series are added; 0.00001-100 gr Mg ions with anions of the halogen series are added; 0.00001-100 gr Sr ions with anions of the halogen series are added.

Example 4: Preparation of a Molecule of a Biologically Active Substance Having a Molecular Weight of about 400 Daltons with Possible Central Double Negative Charge and Possibility of 4 Lateral Hydrogen Bridges Ingredients:

| | |
|---|---|
| Osmotized water | gr 1000.00000 |
| Sodium alginate | gr 2.50000 |
| Phosphoric acid | gr 1.50000 |
| Sodium hydroxide | q.s. pH 5.75 |
| Gluconolactone | gr 0.10000 |
| Hydroxyethyl cellulose | gr 0.20000 |
| Inulin | gr 0.75000 |
| Methylglucose distearate | gr 0.10000 |
| Biologically active subst.: | % depending both on the molecular weight and the surface charges and possible stereoisomeric configuration |
| D-mannose | gr 0.17000 |
| D-fructose | gr 0.65000 |
| Calcium hydroxide | gr 0.00015 or q.s. up to pH 6.02 |
| Anhydrous magnesium chloride | gr 0.00015 |
| Anhydrous calcium chloride | gr 0.00015 |

Preparation:

2.5 gr sodium alginate are added to one liter of osmotized water brought to 40.3° C.; complete dissolution is reached in 1 h.

Then the hydrolysis step is started. 1.5 gr $H_3PO_4$ are added and vigorous stirring is effected for 4 h; cooling to 22° C. is effected and the pH is controlled by adjusting it to 5.75 by means of NaOH.

Thereafter, the assembling step is carried out. 0.1 gr gluconolactone, 0.2 gr HEC, 0.75 gr inulin and 0.1 gr methylglucose distearate are added. Temperature is adjusted to 40° C. and mixing under very vigorous stirring is effected for 12 h. Temperature is brought back to 20° C. 20 gr of a biologically active substance are added and mixing is carried out for 2 h at 22° C. 0.17 gr mannose and 0.65 gr fructose are added. 0.00005 gr $Ca(OH)_2$ are added and the direction of rotation is reversed. 0.00010 gr $Ca(OH)_2$ are added.

0.00015 gr MgCl$_2$ and 0.00015 gr CaCl$_2$ are added. The pH is brought to 6.02 by adding microamounts of Ca(OH)$_2$ under slow stirring.

Example 5: In Vivo Experiment—Administration of Iron Bisglycinate

The process for obtaining a system for controlled delivery of a biologically active substance was used for administering iron bisglycinate to mice, which were then sacrificed and examined for verifying assimilation of iron by the enterocytes of the intestine.

In a mixer, 2.65 gr sodium alginate were added to one liter of water at 50° C.; compete dissolution is reached in 3 h. 0.20 gr mannose and 1 mL phosphoric acid were then added. At a later stage, 1.18 gr hydroxyethyl cellulose were added so as to obtain a mixture containing the various components with the following ratios:

Sodium alginate 0.25:Mannose 0.5:Hydroxyethyl cellulose 0.23.

It is to be noted that in this example mannose has been added to the starting sodium alginate in order to prevent oxidation of iron during the making of the "box".

The mixture was mixed to phosphoric acid at 50° C. for 24 hours. The addition of phosphoric acid led on one hand to depolymerization of alginate and formation of flat structures of G blocks and M blocks (see FIG. 2b) and on the other hand to phosphorylation of mannose and formation of P-mannose.

Advantageously, the presence of P-mannose contributes to confer biomimetic properties to the "box" obtained with the process according to the invention, which properties promote the process of endocytosis/transcytosis by the enterocytes of the organism.

The mixture was buffered with NaOH for interrupting acid digestion and bring the pH to 6.2 and was cooled to 22° C.

0.08 gr mannose were added and, after 15 minutes, the biologically active substance, i.e. 3.00 gr iron bisglycinate, was introduced. The mixture was stirred at room temperature for 1 h.

Subsequently, 0.6 mL CaCl$_2$ 18 mM, 0.34 mL MgCl$_2$ 18 mM, 1.36 gr mannose, 1.23 gr methyl ethyl cellulose and 0.38 gr hydroxyethyl cellulose were added. After reversing the direction of rotation of the mixer, 1 mL lime milk (CaOH)$_2$ (SS) and the mixture was stirred for further 3 h.

In this way, closing of the boxes was obtained.

Finally, in order to stabilize density of the suspension of "micro-boxes" to be administered to mice by gavage, 0.02 gr guar gum were added.

Figure 7:
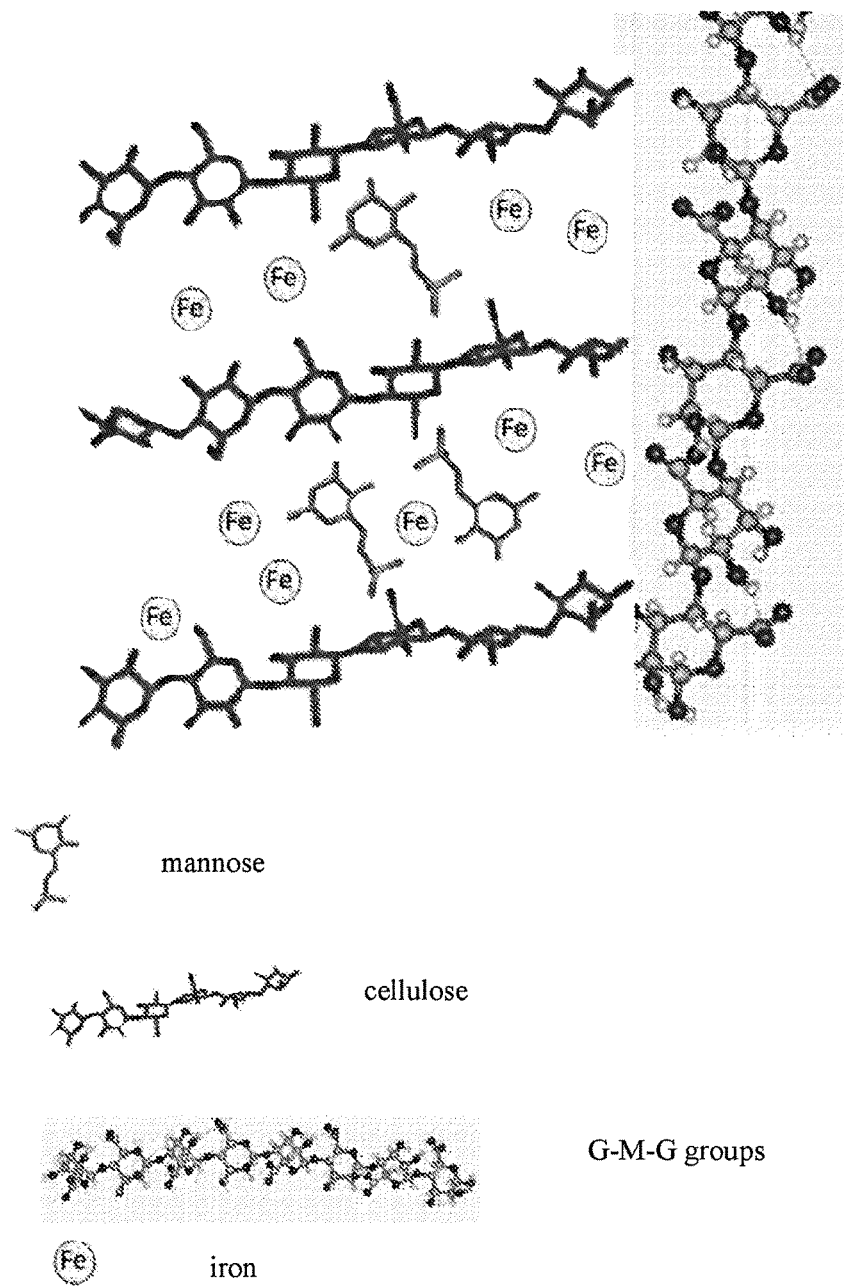
FIG. 7 schematically shows the tridimensional structure of a structure or "box" obtainable in an example of application of the process according to the invention.

FIG. 7 schematically shows the obtained structure.

Figure 8A:
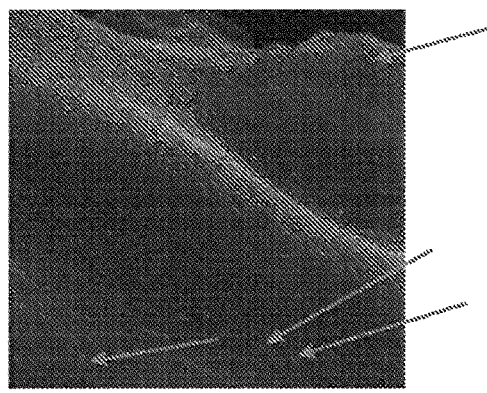
FIGS. 8a-8e show the assimilation of a biologically active substance delivered by the controlled delivery system according to the invention.
Figure 8B:
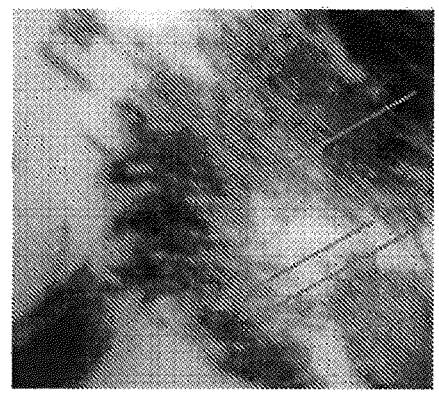
Figure 8C:
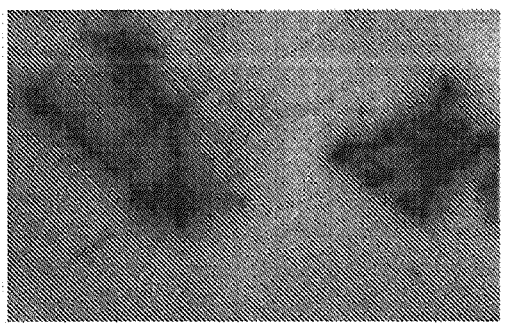
Figure 8D:
Figure 8E:
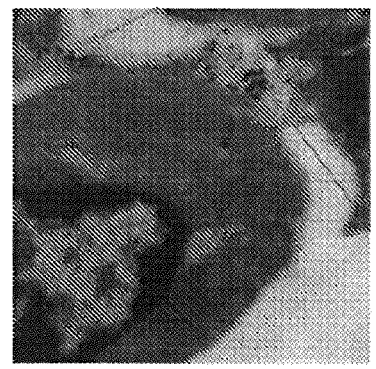

FIGS. 8a-8e are electron microscope images showing assimilation of iron (biologically active substance) by the mice:

in FIG. 8a the arrows indicate the "box-like" structures on a cellulose substrate;

FIG. 8b shows the "box-like" structures in the gastric tract of a mouse; the arrows indicate iron, which is shown as a group of electron dense points;

FIG. 8c shows the "box-like" structures in the intestinal lumen of a mouse; the "box-like" structures open and the iron particles (indicated by the arrows) appear to be condensate, with weakly electron dense material around them;

FIG. 8d shows an enterocyte of a mouse with iron-containing transcytotic vesicles;

FIG. 8e shows how—1 hour after administration through the oral route—iron has been transferred to the blood vessel.

From the above disclosure it is apparent that the invention achieves the objects set forth above, as it provides a process for obtaining a system for the controlled delivery of a biologically active substance which can adapt to a large variety of different substances (ions, molecules, macromolecules, . . . ) and allows to remarkably enhance the efficiency of the delivery of the carried substance.

It is further apparent that the description provided herein has been given by way of non-limiting example and that several modifications and variants within the reach of the person skilled in the art will in any case fall within the scope of the invention as defined in the appended claims.

For example, while in the preceding detailed description reference has been made to applications to biologically active substances that can be administered through the oral route, it is understood that the controlled delivery system of the present invention might be profitably used as well in applications to biologically active substances that can be administered through different routes, for example parenterally or for topic use.

The invention claimed is:

1. A process for obtaining a system for the controlled delivery of a biologically active substance, comprising the steps of:

providing one or more alginates;

submitting the one or more alginates to a hydrolysis process in acid medium, whereby polymeric chains of guluronic acid groups and mannuronic acid groups resulting from said hydrolysis of the one or more alginates are obtained;

adding monomers or polymers derived from cellulose substituted with functional groups;

cleaving the monomers or polymers derived from cellulose substituted with functional groups into cellulosic monomers or dimers, whereby the cellulosic monomers or dimers form bridges for linking the polymer chains of guluronic acid groups and mannuronic acid groups;

adding the biologically active substance, the active substance being assembled to the polymeric chains of guluronic acid groups and mannuronic acid groups and to the cellulosic monomers or dimers forming the bridges by electrostatic interactions;

adding a polymerizing agent and carrying out polymerization, whereby the polymerization generates flat structures consisting of the polymeric chains of guluronic acid groups and mannuronic acid groups and the bridges made of cellulosic monomers or dimers are interposed between the flat structures; and adding mannose accompanied by a polymerizing agent, whereby the mannose, along with the flat structures formed by the polymeric chains of guluronic acid groups and mannuronic acid groups and with the bridges between the flat structures formed by the cellulosic monomers or dimers, completes a three-dimensional structure enclosing the active substance, whereby, when the mannose shifts from a closed form to an open form, the three-dimensional structure is opened and the biologically active substance is delivered.

2. The process according to claim 1, further comprising the step of adding a gelling agent.

3. The process according to claim 1, further comprising the step of adding one or more substances chosen from the group comprising gluconolactone, methylglucose distearate, galactose, gluconic acid, gluconic acid salts, gluconic acid esters or combinations thereof.

4. The process according to claim 1, wherein the hydrolysis process in acid medium is carried out by adding an organic or inorganic polyprotic acid.

5. The process according to claim 4, wherein the polyprotic acid is phosphoric acid.

6. The process according to claim 4, wherein the polyprotic acid is lactic acid.

7. The process according to claim 1, wherein the polymerizing agent is a divalent ion.

8. The process according to claim 2, wherein the gelling agent is a polysaccharide.

9. The process according to claim 1, wherein the biologically active substance is provided as ions, molecules or macromolecules.

10. The process according to claim 9, wherein the biologically active substance is provided as ions and wherein the biologically active substance is separated and selected before the step of adding the biologically active substance.

11. The process according to claim 7, wherein the polymerizing agent is a calcium ion ($Ca^{2+}$).

12. The process according to claim 8, wherein the gelling agent is inulin or cellulose and/or its derivatives.

* * * * *